United States Patent [19]
Kerin et al.

[11] Patent Number: 5,873,815
[45] Date of Patent: Feb. 23, 1999

[54] ACCESS CATHETER AND METHOD FOR MAINTAINING SEPARATION BETWEEN A FALLOPOSCOPE AND A TUBAL WALL

[75] Inventors: John Kerin, North Adelaide, Australia; Charles Milo, Santa Barbara, Calif.; Julian N. Nikolchev, Portola Valley, Calif.; James Doty, Larkspur, Calif.; Dai T. Ton, San Jose, Calif.; Richard Hill, Berkeley, Calif.; Marc Schraner, Pacifica, Calif.; Tom Kramer, San Carlos, Calif.

[73] Assignee: Conceptus, Inc., San Carlos, Calif.

[21] Appl. No.: 879,661

[22] Filed: Jun. 23, 1997

Related U.S. Application Data

[63] Continuation-in-part of Ser. No. 544,384, Oct. 10, 1995, Pat. No. 5,716,321.

[60] Provisional application No. 60/021,130 Jun. 28, 1996.

[51] Int. Cl.$^6$ .................................................. A61B 1/01
[52] U.S. Cl. ..................... 600/114; 600/127; 600/135; 604/208
[58] Field of Search ...................... 600/104, 116, 600/127, 114, 115, 129, 585; 604/280, 264, 95, 96

[56] References Cited

U.S. PATENT DOCUMENTS

| | | |
|---|---|---|
| 1,556,355 | 10/1925 | Roney ...................................... 600/104 |
| 1,621,159 | 3/1927 | Evans . |
| 3,866,601 | 2/1975 | Russell . |
| 4,198,960 | 4/1980 | Utsugi . |
| 4,306,566 | 12/1981 | Sinko . |
| 4,350,147 | 9/1982 | Sarrine . |
| 4,608,965 | 9/1986 | Anspach, Jr. et al. . |
| 4,717,387 | 1/1988 | Inoue et al. . |
| 4,779,611 | 10/1988 | Grooters et al. . |
| 4,793,326 | 12/1988 | Shishido . |
| 4,825,259 | 4/1989 | Berry, Jr. . |
| 4,846,812 | 7/1989 | Walker et al. . |
| 4,878,893 | 11/1989 | Chin . |
| 5,047,848 | 9/1991 | Krauter . |
| 5,099,827 | 3/1992 | Melzer et al. . |
| 5,263,928 | 11/1993 | Trauthen et al. . |
| 5,279,596 | 1/1994 | Castaneda et al. . |
| 5,306,261 | 4/1994 | Alliger et al. . |
| 5,307,814 | 5/1994 | Kressel et al. . |
| 5,308,342 | 5/1994 | Sepetka et al. . |
| 5,358,496 | 10/1994 | Oritz et al. . |
| 5,385,152 | 1/1995 | Abele et al. . |
| 5,505,686 | 4/1996 | Willis et al. . |
| 5,746,692 | 5/1998 | Bacich et al. ........................... 600/104 |
| 5,749,883 | 5/1998 | Halpern .................................. 600/114 |
| 5,807,236 | 9/1998 | Bacich et al. ........................... 600/104 |

OTHER PUBLICATIONS

Kerin et al., "Falloposcopy: A Microendoscopic Technique for Visual Exploration of the Human Fallopian Tube form the Uterotubal Ostium to the Fimria Using a Transvaginal Approach, " *Fertility and Sterility*, vol. 54, No. 3, pp. 390–400 (1990).

Kerin et al., "Development and Application of a Falloposcope for Transvaginal Endoscopy of the Fallopian Tube, " *J. Laparoendoscopic Surgery*, vol. 1 pp. 47–56.

*Primary Examiner*—John P. Leubecker
*Attorney, Agent, or Firm*—Townsend and Townsend and Crew LLP

[57] ABSTRACT

A method and apparatus are provided for imaging a narrow body lumen, the method comprising maintaining separation between a distal end of an optical viewing scope and a lumen wall with a spacing structure which extends distally from the distal end of an access catheter. Optional spacing structures include distal cages and a guidewire which is fixed to and extends distally from the access catheter body. The invention is beneficial during either retrograde imaging of the fallopian tube, and also allows antigrade imaging and advancing the access catheter and scope under the direction of the image provided, as it prevents the tubal wall from coming into such close proximity to a falloposcope as to produce "white-out" on the imaging monitor.

12 Claims, 13 Drawing Sheets

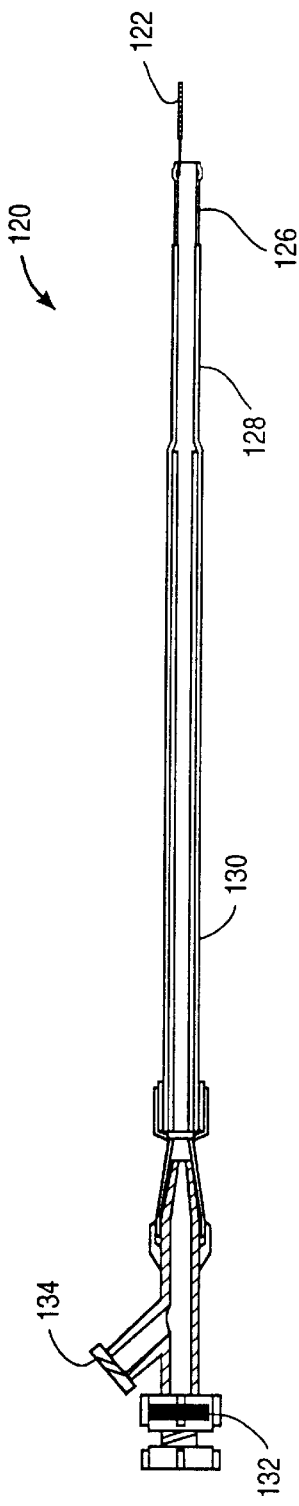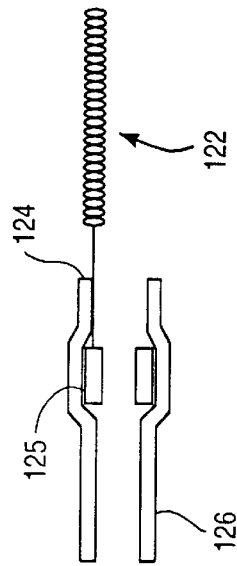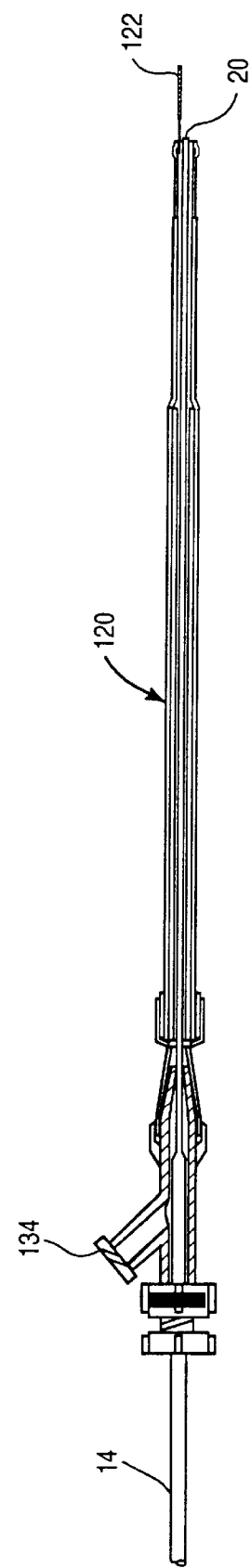

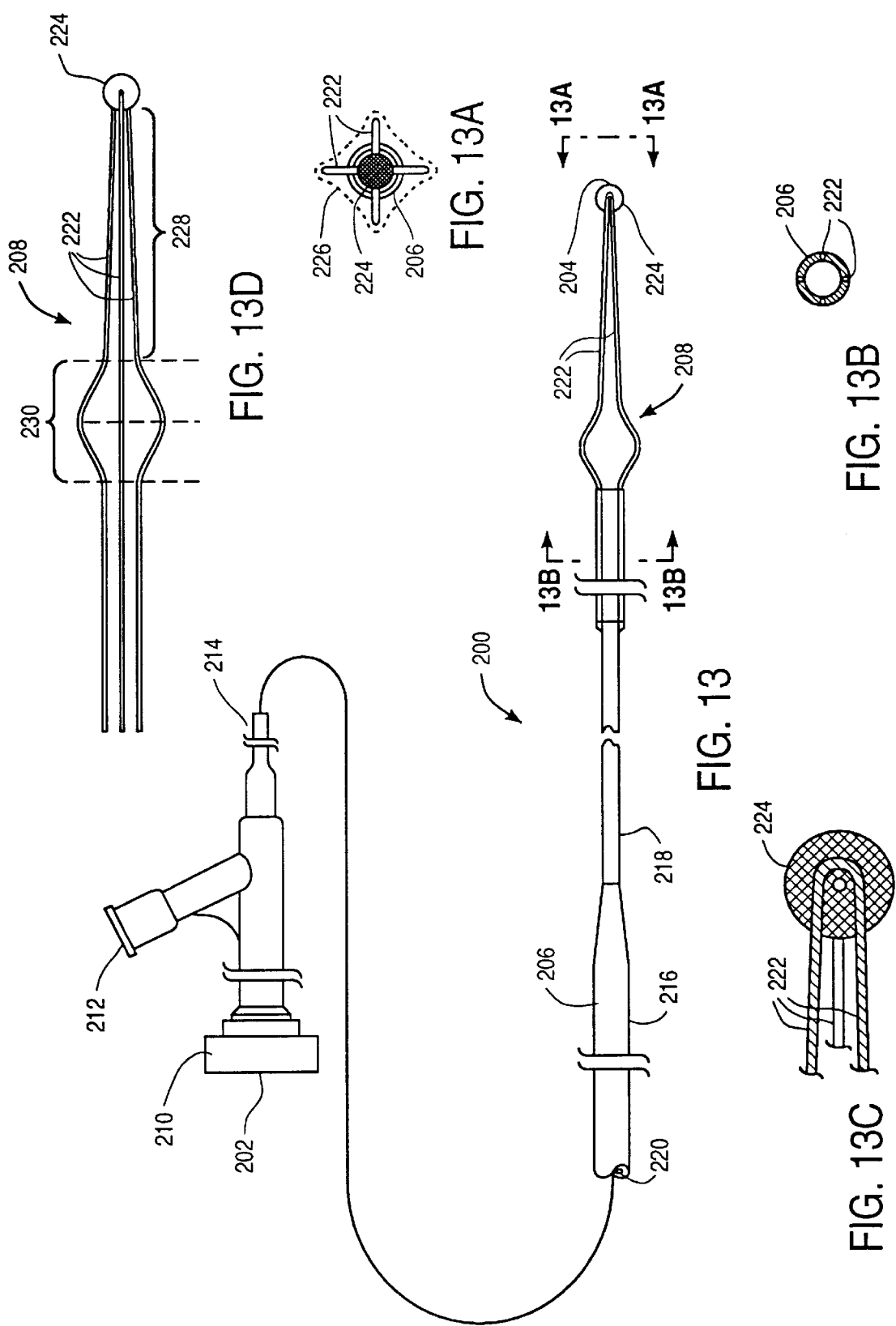

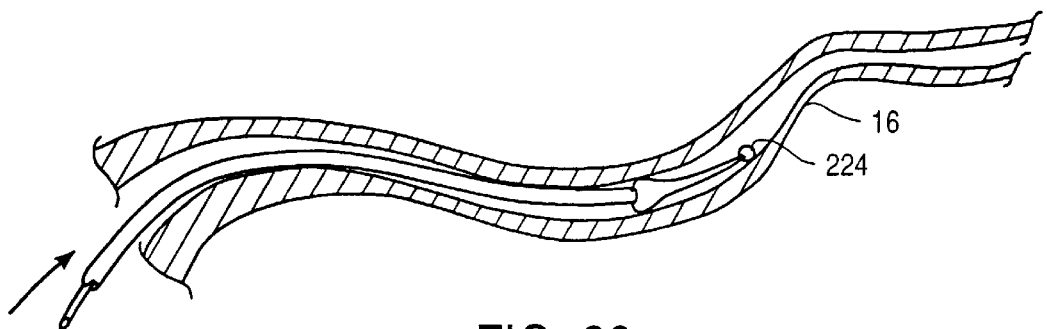
FIG. 20
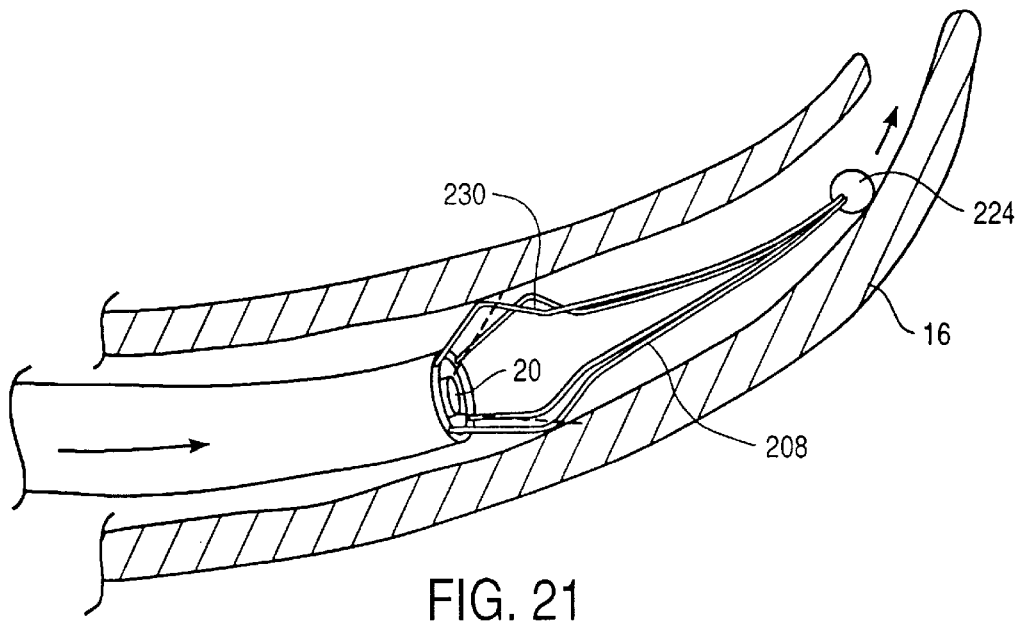
FIG. 21
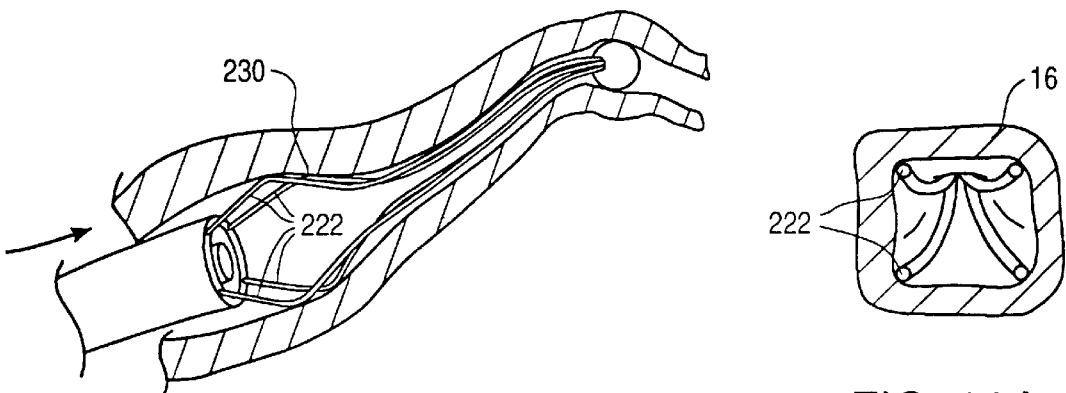 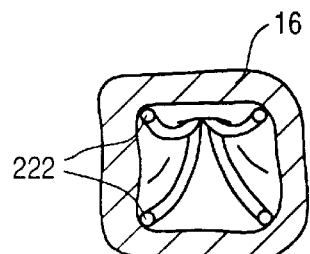
FIG. 22  FIG. 22A

ACCESS CATHETER AND METHOD FOR MAINTAINING SEPARATION BETWEEN A FALLOPOSCOPE AND A TUBAL WALL

CROSS REFERENCE TO RELATED APPLICATIONS

This application is related to, and claims the benefit of priority from, U.S. Provisional Patent Application Ser. No. 60/021,130, filed Jun. 28, 1996, and is a continuation-in-part of U.S. Patent Application Serial No. 08/544,384, filed Oct. 10, 1995, now U.S. Pat. No. 5,716,321 the full disclosures of which are incorporated herein by reference.

BACKGROUND OF THE INVENTION

1. Field of the Invention

The present invention relates generally to endoscopic surgical methods and apparatus. More particularly, the present invention provides an access catheter having a distally protruding structure which maintains separation between a viewing scope and a lumenal wall.

Diseases of the fallopian tubes are a major cause of infertility and tubal pregnancy. Until recently, diagnosis and treatment of tubal disease has been hampered by the difficulty in accessing and imaging the interior of the fallopian tube. Such difficulties, however, have been largely overcome by the recent availability of very small guidewires, catheters, and fiberoptic viewing scopes, usually referred to as falloposcopes. Using these instruments and systems, a physician can gain atraumatic access to the interior of the fallopian tube through a hysteroscope positioned within the uterus. Such falloposcopic imaging techniques were described by Kerin et al. in *Fertil. Steril.*, Vol. 54, pp. 390–400 (1990), and in *J. Laparoendoscopic Surg.*, Vol. 1, pp. 47–56.

Falloposcopic access and imaging techniques are generally performed as follows. A hysteroscope is positioned within the uterus and an irrigating solution is introduced to distend the uterus and permit video monitoring. A very small guidewire is then introduced through the hysteroscope and advanced past the ostium and into the fallopian tube. The guidewire will continue to be advanced until it approaches the distal fimbria. A small tubular access catheter may then be advanced through the hysteroscope and over the guidewire into the fallopian tube, again preferably approaching the distal fimbria. After removing the guidewire, the falloposcope (which is a small diameter fiberoptic bundling including both imaging and illumination fibers in a single shaft) is advanced until its distal end reaches the distal end of the access catheter. Imaging may then be performed in a retrograde manner with the falloposcope and access catheter being drawn outwardly together through the fallopian tube while producing an image on the associated video monitor. The lumen of the tubular access catheter will also provide an access path for devices, such as drug delivery catheters, small instruments, and the like, for treatment of tubal lumen disease.

While such retrograde falloposcopic imaging techniques represent a significant improvement, they still suffer from certain limitations. In particular, falloposcopes having both illumination and imaging fiberoptics require a minimum separation between the imaging lens at the end of the fiberoptic bundles and the tissue to be imaged. Unfortunately, the narrowly confined lumen of the fallopian tube contracts soon after the access catheter has been withdrawn. Hence, the tubal wall often collapses in on the withdrawing falloposcope during retrograde imaging, intruding upon the required imaging separation. As the tubal wall tissues come in close proximity with the imaging and illumination fiberoptics, excessive illumination light is reflected back to the imaging system, causing a partial or total "white-out" of the viewing monitor. These white-outs are a common and undesirable limitation on the effectiveness of retrograde imaging of the fallopian tube and other narrow body lumens.

It would therefore be desirable to provide improved methods and systems for imaging fallopian tubes and other narrow body lumens. It would be particularly desirable to provide improved access catheters and methods for their use which would reduce the incidence of white-out associated with the fallopian tubal wall approaching too close to the optical viewing scope. It would further be desirable if such improved methods and devices were compatible with and able to enhance the effectiveness of retrograde tubal imaging systems and methods.

It would also be desirable to provide improved imaging access methods, devices, and systems for use in the fallopian tubes and other body lumens. It would be particularly advantageous to provide simplified, atraumatic imaging methods and systems which would reduce the time and complexity of known fallopian tube accessing and imaging techniques, and which would provide reliable, high quality images of tubal walls to assist in the diagnosis and therapy of tubal disease.

2. Description of the Background Art

Kerin et al., *Fertil. Steril.*, Vol. 54, pp. 390–400 (1990), and in *J. Laparoendoscopic Surg.*, Vol. 1, pp. 47–56, have been described above. U.S. Pat. No. 4,793,326 describes an industrial endoscope having an elongated arm member to facilitate advancing separate illumination and observation windows past the abrupt steps of piping elbow joints. U.S. Pat. No. 4,717,387 describes an intercardiac catheter having a distal balloon for positioning the catheter with respect to a body surface to be viewed through an optical scope. U.S. Pat. No. 5,263,982 describes an endoscopic catheter having a laterally offset movable guidewire.

U.S. Pat. Nos. 5,047,848 and 4,825,259 disclose baroscope having specialized distal tip gauges which permit optical measurements of imaged features. U.S. Pat. No. 4,608,965 discloses an endoscopic sheath having a Malecott-type structure for anchoring the scope in a body cavity.

U.S. Pat. No. 5,358,496 is representative of numerous instruments intended to be inserted through endoscopes. U.S. Pat. Nos. 3,866,601; 4,306,566; 4,350,147; 4,846,812; 5,099,827; 5,263,928; 5,279,596; 5,306,261; 5,307,814; 5,308,342; 5,385,152; are also relevant.

An exemplary falloposcopic imaging system is described in co-pending application Ser. No. 08/207,475 filed Mar. 7, 1994, the full disclosure of which is incorporated herein by reference.

SUMMARY OF THE INVENTION

In a first aspect, the present invention provides a method for viewing a lumenal wall of a narrow body lumen. The method of the present invention comprises introducing a catheter within a body lumen and positioning an optical viewing scope within a lumen of the catheter so that a distal end of the scope is at a scope viewing position adjacent to a distal end of the catheter. A spacing structure is positioned between the lumenal wall and the distal end of the scope maintains separation between the lumen wall and the scope. The lumenal wall is imaged through the scope while the spacing structure maintains separation between the distal end of the scope and the lumenal wall. This separation helps prevent imaging white-out conditions which might otherwise occur when the optical viewing scope and body lumen wall are in close proximity. Although the spacing structure will typically appear in the viewing monitor, blocking some portion of the lumen wall from imaging, the image quality and availability are substantially enhanced. Preferably, the catheter is advanced distally of a target region of the body lumen during the introducing step, and the catheter and scope are proximally withdrawn while imaging through the distally oriented scope. This is generally referred to as "retrograde imaging."

In some embodiments, the imaging step comprises viewing the lumen wall at least in part through a cage disposed over the distal end of the scope. Alternatively, the spacing structure may comprise a guidewire which extends distally from the catheter, which guidewire may also be rotated during introduction of the catheter to maneuver the catheter through a body lumen system. Alternatively, the spacing structure may comprise a wire loop extending distally from the catheter body. Such a wire loop may be expanded by advancing a proximal length of the wire relative to the proximal end of the catheter. In this way, the size of the loop can be adjusted maintain separation between the body lumen wall and the optical viewing position.

In another aspect, the present invention provides an improved method for viewing a target region of a fallopian tube. The method is of the type including transcervically accessing the fallopian tube with the catheter and inserting an optical viewing scope within a lumen of the catheter so that distal ends of the scope and catheter are adjacent to each other, and then retrograde imaging the fallopian tube by withdrawing the scope and catheter together. The improvement comprises promoting axial alignment between the tubal wall and the distal end of the scope with a structure extending distally from the distal end of the catheter. Axial alignment between the distal end of the scope and the tubal wall will optionally comprise axially rotating the catheter to engage the structure against the tubal wall, where the structure is unsymmetrical about an axis of the catheter lumen. Advantageously, such an unsymmetrical spacing structure can be used to selectively engage only that portion of the tubal wall which is necessary to avoid a white-out. The unsymmetrical spacing structure further avoids blocking of the imaging view where not required to prevent intrusion of the tubal wall toward the viewing scope.

In another aspect, the present invention provides a catheter for viewing a wall of a narrow body lumen, the catheter for use in combination with an optical viewing scope of the type including both illumination fibers and viewing fibers. The catheter comprises an elongate tubular body having a proximal end, a distal end and a central lumen therebetween. The lumen slidably receives the shaft of the scope to a scope viewing position adjacent to the distal end of the body. Additionally, a spacing structure extends distally from the distal end, usually being fixed or coupled thereto, so as to separate the scope viewing position from the lumen wall. Advantageously, the catheter of the present invention need only include a single axial lumen, thereby minimizing its cross-sectional size. Preferably, the spacing structure is affixed with a coupler ring which fittingly engages the body, the coupler ring ideally being disposed within the body lumen and having an outer diameter which is larger than a relaxed lumen diameter. In some embodiments, the spacing structure comprises a cage disposed over the scope viewing position. The cage may comprise a distal extension of the body having a plurality of viewing slots, or may alternatively comprise a separate structure attached to the distal end of the catheter.

In some embodiments of the catheter of the present invention, the spacing structure comprises a guidewire which extends distally of the body, typically being cantilevered from the distal end of the catheter at the edge of a distal lumen opening. Ideally, the guidewire comprises a coiled distal section and an uncoiled section between the catheter and coil. This provides an increasing distal flexibility comparable to that of distally tapering guidewires, but with a decrease in proximal guidewire cross-section. The flexibility of the guidewire is ideally similar to tapered guidewires sold under the tradenames "Traveler" and "Robust" by Conceptus, Inc. of San Carlos, Calif., the present assignee. The guidewire may thus find use in maneuvering the catheter through the body lumen, and may also allow the catheter to be advanced while "antigrade" imaging through a scope at the scope viewing position. Such antigrade imaging will potentially provide a means for directing the catheter distally, and also provide a simultaneous image of the tubal wall. Alternatively, the spacing structure may comprise an expandable distal loop actuable by advancing a proximal portion or extension of the loop relative to the proximal end of the body. This provides a controllable separation between the lumen wall and the scope viewing position to overcome white-out conditions as they are encountered along the body lumen. As a further alternative, the spacing structure comprises one or more diagonal tips extending from the distal end of the body.

In yet another aspect, the present invention provides a method for viewing a luminal wall of a narrow body lumen, the method comprising introducing a catheter into the body lumen, the catheter having an access lumen and a distal spacing structure. An optical viewing scope is positioned through the access lumen of the catheter. The scope images the luminal wall through the spacing structure while the spacing structure maintains separation between the distal end of the scope and the luminal wall. Generally, imaging is performed through openings defined by discreet structural elements of the spacing structure, the spacing structure typically comprising a perforate cage. Ideally, the cage flexes to accommodate bends in the body lumen, and includes a large, rounded, distally oriented surface that promotes tracking of the cage and access catheter along the body lumen when the catheter advances axially therein. The cage optionally helps to center the scope within the body lumen, and may also distend the body lumen to facilitate viewing of the inner surface of the luminal wall. Advantageously, such a caged structure will allow safe and effective antigrade imaging of narrow body lumens (such as the fallopian tube) by carefully controlling the relative positions of the scope and portion of the surrounding luminal wall.

In yet another aspect, the present invention provides a catheter for viewing a wall of a narrow body lumen. The catheter of the present invention will be used in combination with an optical viewing scope, the catheter comprising an elongated tubular body having a proximal end, a distal end, and a lumen therebetween. A spacing structure with a plurality of cage elements extends distally from the distal end of the tubular body, the spacing structure adapted to maintain separation between the scope and the surrounding luminal wall when the scope images the body lumen between the cage elements. Preferably, the spacing structure is adapted to track along the body lumen when axially advanced therein, typically having at least an axial portion which is flexible, and a tracking tip which provides a large, rounded distally oriented surface. Ideally, the axial elements comprise a super-elastic shape memory alloy such as Nitinol™.

In yet another aspect, the present invention provides a fallopian tube viewing system for imaging a tubal wall of the fallopian tube, the viewing system comprising a falloposcope having a proximal end, a distal end, and an axis therebetween. The access catheter has an elongate tubular body with a proximal end, a distal end, a lumen therebetween which slidably receives the falloposcope. A flexible separation structure extends distally from the distal end of the body to maintain separation between the scope and the surrounding tubal wall when the scope is disposed within the lumen of the access catheter, when the scope and catheter are disposed within the fallopian tube, and when the body lumen is imaged through the scope through the separation structure.

In yet another aspect, the present invention provides a method for manufacturing a caged access catheter, the method comprising attaching a plurality of flexible elongate cage elements to each other at a junction. A tracking tip is formed at the junction, the tracking tip having a rounded surface which is larger than the combined cross-sections of the cage elements. The cage elements are affixed about a lumen of a tubular body so that the elongate elements extend distally from the tubular body.

BRIEF DESCRIPTION OF THE DRAWINGS

FIGS. 10A, B and C illustrate a preferred access catheter having a distal guidewire for maintaining axial alignment and separation between a falloposcope and a surrounding fallopian tube.

FIGS. 13–13D illustrate a preferred embodiment of a caged access catheter having flexible cage elements and a tracking tip with a rounded distal surface to improve trackability, particularly during antigrade imaging of tortuous narrow body lumens such as the fallopian tubes.

FIGS. 20–22A illustrate the enhanced trackability provided by the distal rounded surface and the axially flexible cage of the preferred access catheter of FIG. 13.

DETAILED DESCRIPTION OF THE SPECIFIC EMBODIMENTS

The present invention provides systems, devices, and methods for accessing and imaging narrow body lumens for the diagnosis and treatment of lumenal disease. The techniques and apparatus of the present invention will generally make use of small optical viewing scopes having both imaging and illumination capabilities, and will maintain separation between the scopes and the lumenal wall to enhance image quality and reliability. In some embodiments, the structures and methods will also help align the lumenal wall relative to the scope for effective viewing.

The present invention will have applications for imaging of the vasculature (particularly of the coronary arteries), the ureter, and spinal column. The most immediate application of the present invention, however, will be in trancervical imaging and accessing of the fallopian tubes. Advantageously, the methods and devices of the present invention can promote effective antigrade imaging of these narrow, delicate, tortuous body lumens, allowing positioning to be optically directed, and avoiding the time consuming guidewire positioning and replacement steps of known retrograde tubal access methods.

Figure 1:
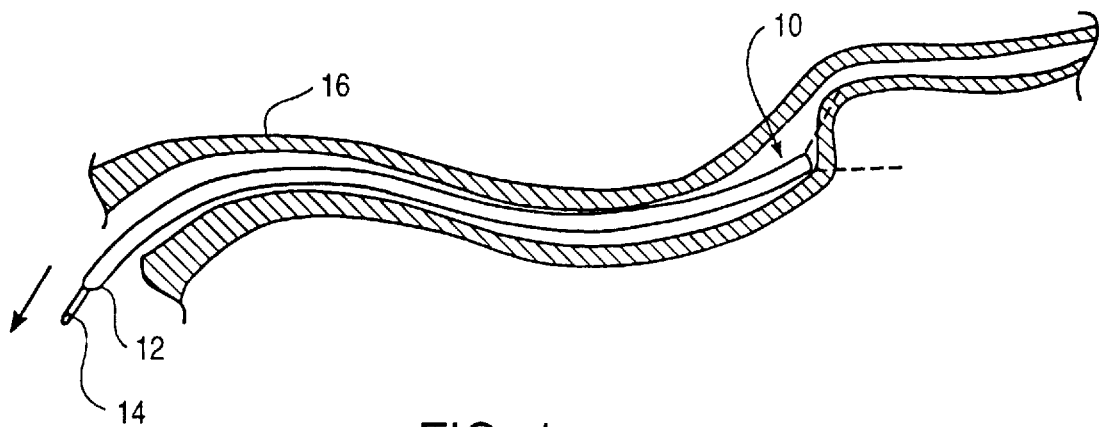
FIG. 1 illustrates a prior art access catheter and optical viewing scope used for retrograde imaging of a fallopian tube.
Figure 2:
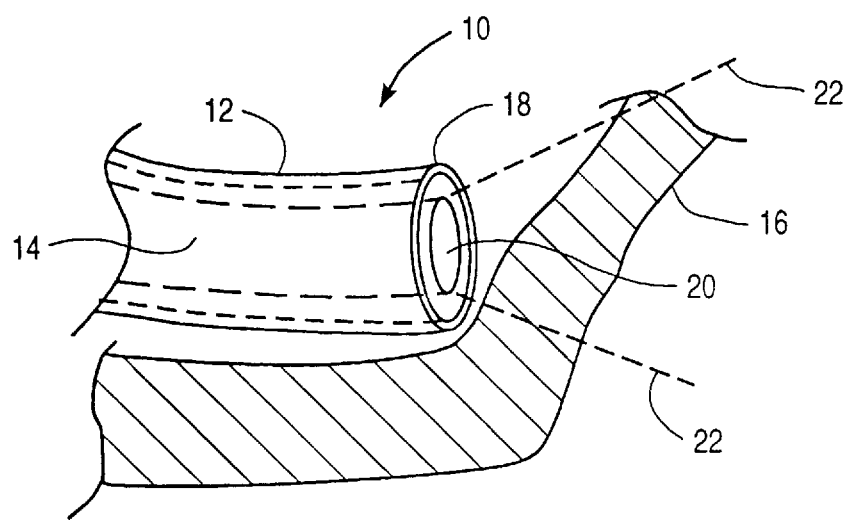
FIG. 2 is a detail view showing the distal ends of the access catheter and optical viewing scope of FIG. 1 in close proximity to the tubal wall, which is typical of the white-out conditions encountered when using the access catheters of the prior art.

Referring to FIGS. 1 and 2, a prior art retrograde fallopian tube viewing system 10 includes an access catheter 12 and a falloposcope 14. Prior art viewing system 10 is inserted to the distal portion of a fallopian tube 16, and is withdrawn proximally as indicated to provide retrograde imaging. Fallopian tube 16 is quite narrow and tortuous, and the tubal wall is highly flexible. Hence, as prior art imaging system 10 is withdrawn proximally, the tubal wall is distended by the access cover 12, and then collapses down to its relaxed shape after a distal end 18 of the access catheter has passed. As optimal imaging occurs when the distal end of the falloposcope is substantially aligned with the distal end of the access catheter, the tubal wall often comes into close proximity with distal end of falloposcope 20.

Falloposcope 14 generally includes two distinct types of optical fibers. The first group of optical fibers is used to transmit light to the distal end of falloposcope 20 to provide illumination for optical viewing. The second type of optical fiber, often comprising a single optical fiber bundle called a "coherent image fiber optic bundle," transmits an optical image from a lens at a distal end of falloposcope 20 to a proximal imaging apparatus. The image itself comprises the illumination light from the illumination fibers which is reflected by objects located within a field of view 22 of distal end of falloposcope 20. As the tubal wall comes into close proximity with both the illumination and optical viewing fibers at the distal end of the falloposcope, the imaging apparatus is unable to produce a coherent picture, and a partial or a total white-out occurs on the viewing monitor.

Figure 3:
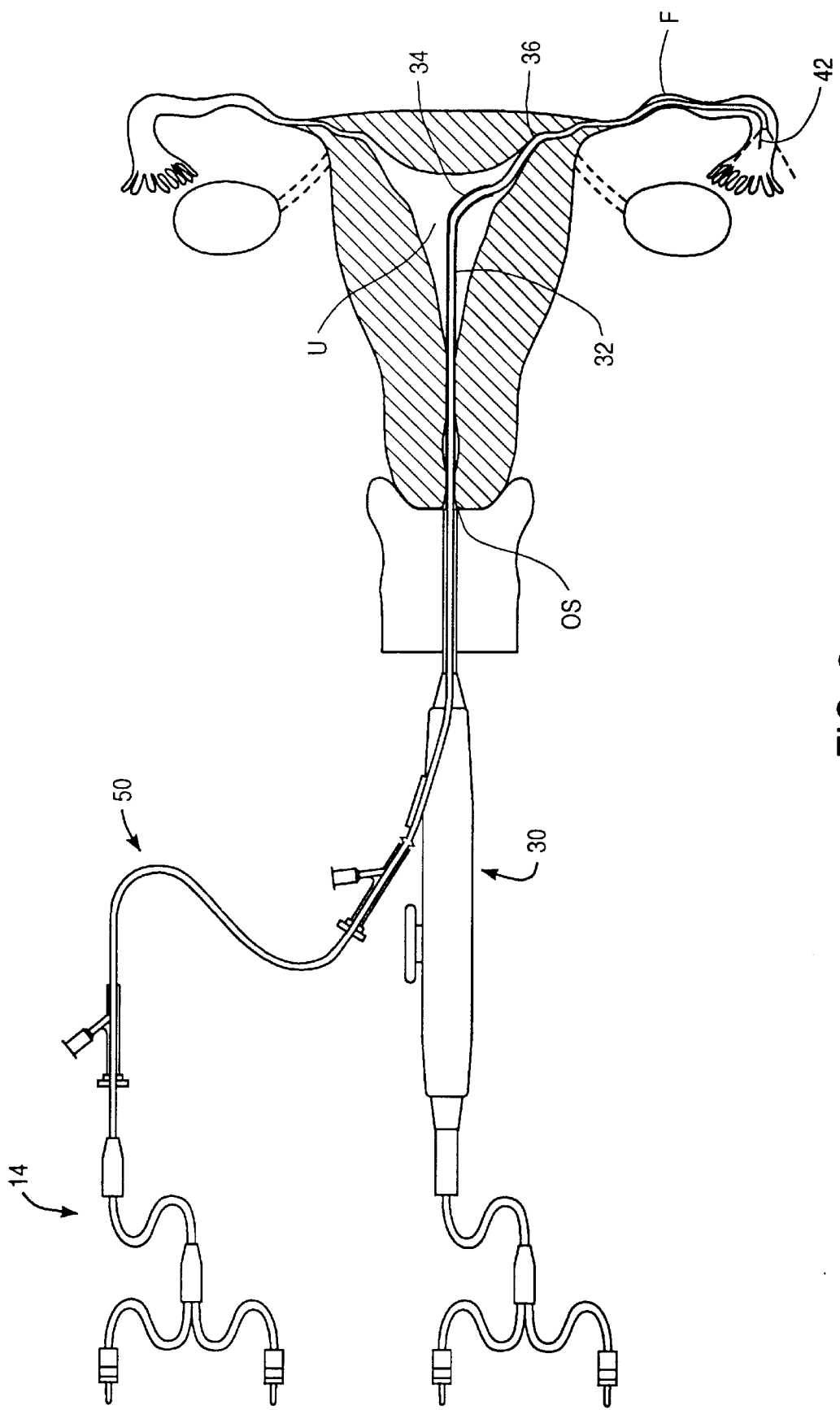
FIG. 3 illustrates a preferred combination of a hysteroscope, access catheter, and falloposcope for use in imaging a fallopian tube, according to the principles of the present invention.
Figure 4:
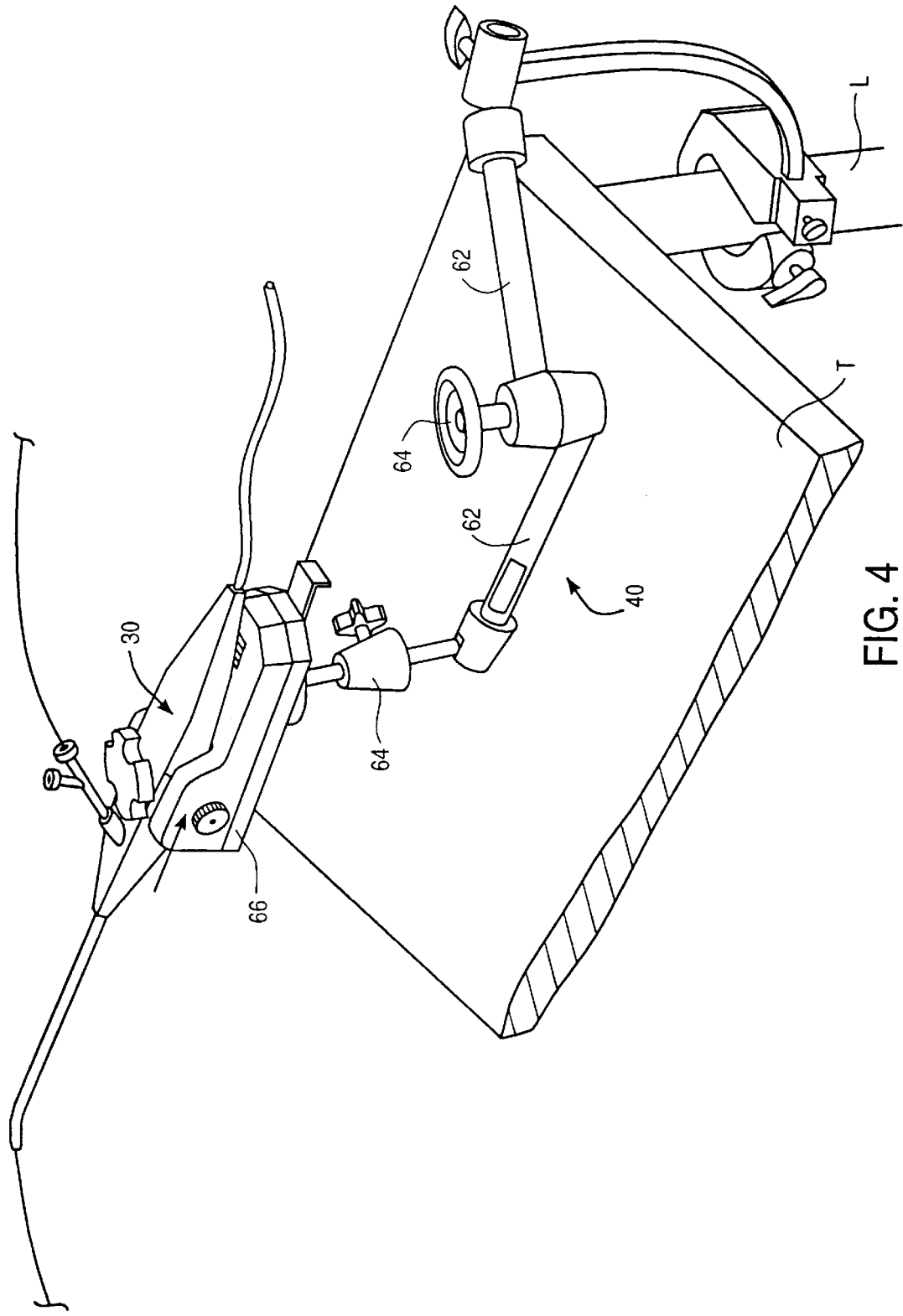
FIG. 4 illustrates a preferred method for supporting the proximal end of the hysteroscope according to the method of the present invention, wherein the proximal end is immobilized by a support structure attached to a table.

A particularly preferred method and apparatus for performing hysteroscopic and falloposcopic procedures, including retrograde imaging, is described in co-pending U.S. patent application Ser. No. 08/207,475, filed Mar. 7, 1994, the full disclosure of which is herein incorporated by reference. As more fully explained in that application, a preferred method for performing falloposcopic procedures makes use of a hysteroscopic viewing scope 30 having a working shaft 32 with a deflectable distal end 34, as shown in FIGS. 3 and 4. Working shaft 32 is introduced to the uterus U, ideally using an adjustable support system 40. Deflectable distal end 34 is directed toward an ostium 36 of fallopian tube F. The uterus will be distended by introduction of irrigation fluid so that a guidewire may be directed into the fallopian tube using visualization through hysteroscope 30. Optionally, the guidewire 42 is disposed at the distal end of a catheter, as described hereinbelow. Alternatively, a conventional guidewire is first introduced to the fallopian tube, so that an access catheter 50 may be advanced over the guidewire in a conventional manner. Where such a conventional guidewire is used, it must generally be removed from a central lumen of positioned access catheter 50 to make room for falloposcope 14.

In order to further simplify the falloposcopic procedures of the present invention, support structure 40 immobilizes the viewing scope 30 on a table T or other surface, once the scope has been properly positioned in the uterus. Support structure 40 includes a plurality of arms 62 and joints 64 which are designed to freely articulate so that a support base 66 at a distal end of support structure 40 can be moved freely in space until locked into position. Preferably, the support structure is firmly secured to a table leg L. Such systems commercially available from suppliers such as Lino Manfrotto & Company.

Figure 5:
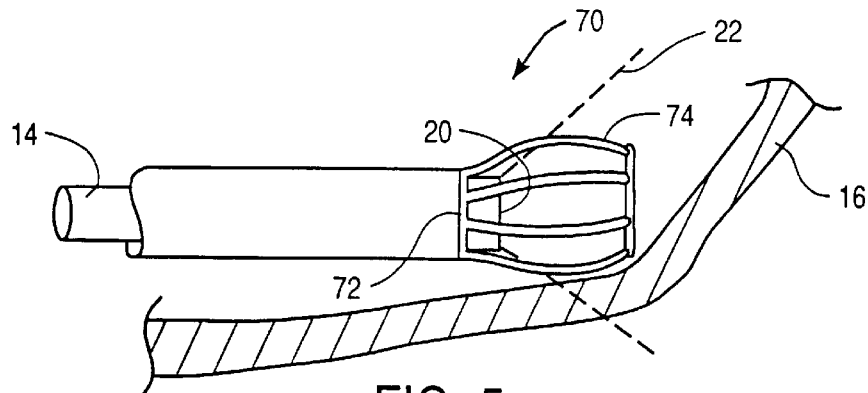
FIG. 5 illustrates a falloposcope which is separated from a tubal wall by an access catheter having a distal cage structure, according to the principles of the present invention.

Referring now to FIG. 5, a caged access catheter 70 slidably receives falloposcope 14 to a scope viewing position at which falloposcope distal end 20 is adjacent to a distal end of the catheter 72. A distal cage structure 74 surrounds distal scope end 20 to prevent the tubal wall of fallopian tube 16 from coming into such close proximity with the distal end of the scope that a white-out occurs.

Distal cage 74 separates the tubal wall from the scope viewing position by any of at least three different mechanisms. First, cage 74 prevents the tubal wall from collapsing immediately after catheter distal end 72 has passed, restraining the tubal wall in its distended position, thereby preventing encroachment of the tubal wall toward the scope. Second, distal cage 74 may reposition the entire distal portion of access catheter 70 away from the tubal wall to provide the necessary separation. Finally, distal cage 74 promotes axial alignment of catheter distal end 72 with the fallopian tube by providing an elongated distal moment arm through which the access catheter and tubal wall engage each other. This also promotes alignment between the falloposcope field of view 22 relative to the orientation of the local fallopian tube axis.

Figure 6:
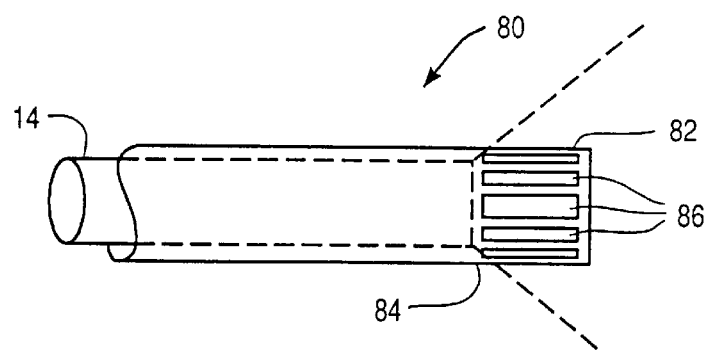
FIG. 6 illustrates an alternative cage structure formed by cutting axial viewing slots in a distal extension of the catheter body.

Referring now to FIG. 6, an alternative caged access catheter 80 is formed with a simplified cage 82. Simplified cage 82 comprises a continuation of the catheter body beyond catheter distal end 84, in which a plurality of viewing slots 86 have been cut. Both caged embodiments of the present access catheter generally provide substantially axisymmetric viewing through an open distal end of the caged structure and through viewing slots 86, or the analogous gaps between the cage structural elements. Rotation of such caged access catheters is generally not necessary to insure separation between the falloposcope and tubal wall, but will allow viewing of tubal wall elements which would otherwise be blocked during at least a portion of the scan.

Figure 7:
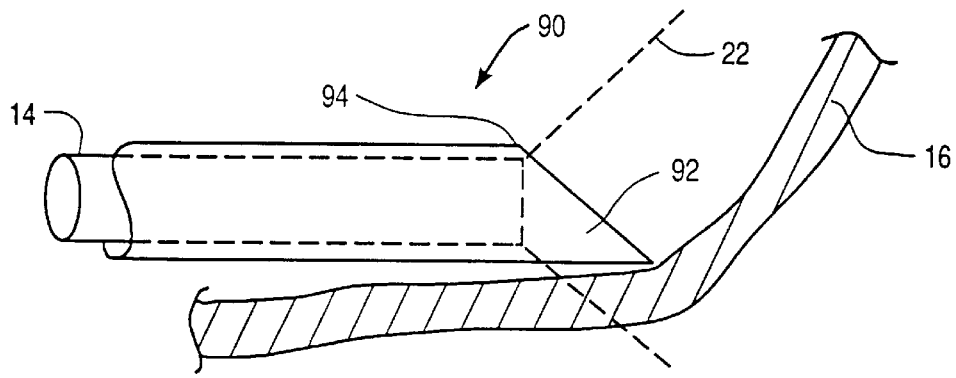
FIG. 7 illustrates a falloposcope which is separated from a fallopian tube wall by an access catheter having a distally protruding diagonal tip, in accordance with the principles of the present invention.
Figure 8:
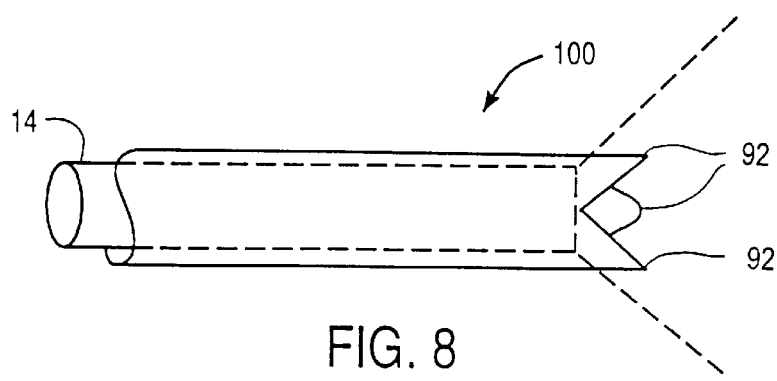
FIG. 8 illustrates an access catheter having a plurality of diagonal tips extending from the distal end of the catheter body, in accordance with the principles of the present invention.

Referring now to FIG. 7, a diagonal tip access catheter according to the present invention comprises a diagonal tip 92 extending distally from catheter distal end 94. It can be seen that diagonal catheter 90 must be rotated so as to engage tubal wall 16 with diagonal tip 92. It can also be seen that the field of view 22 is clear in much of the area where distal structure is not required to engage the tubal wall. The angle of diagonal tip 92 will typically be in the range between 45° and 80° from normal, and need not be constant nor extend the entire catheter width. A multiple angle access catheter 100 reduces the need for rotating the catheter, as seen in FIG. 8.

Figure 9A:
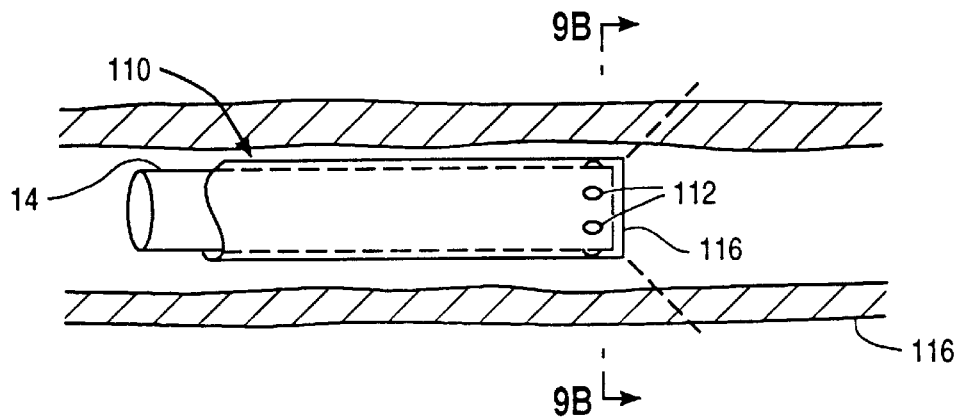
FIGS. 9A and B illustrate an access catheter having a plurality of side openings and a central lumen opening which provide a balanced flow path for irrigation fluid to maintain separation between the falloposcope and the tubal wall.
Figure 9B:
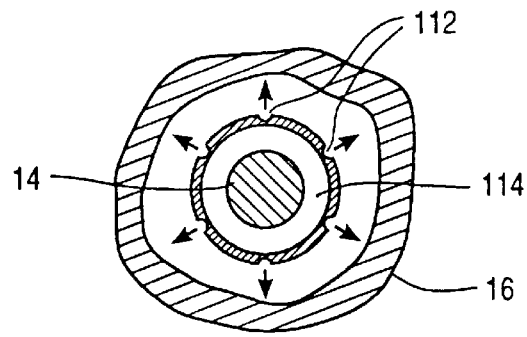

Referring now to FIGS. 9A and B, a fluid separating catheter 110 comprises a plurality of radial distal passages adjacent to the catheter distal tip 116. Radial passages 112 direct clear flush solution against the tubal wall of fallopian tube 16 to promote separation between falloposcope 14 and the tubal wall. Flush solution also flows out the distal tip 116 of fluid catheter 110 around falloposcope 14, thereby promoting separation between the distal end of the falloposcope and the tubal wall. The fluidic paths represented by the radial passages 112, are preferably balanced by varying the sizes of the radial passages relative to the open gap 114 between the catheter and falloposcope at the distal end.

A fixed distal guidewire access catheter 120 will be described with reference to FIGS. 10A through C.

Guidewire catheter 120 comprises a distal guidewire 122 extending distally from a distal end of the catheter body 124, typically by a distance from 0.5 to 5 cm, ideally being 1 to 3 cm long and less than 0.02" in diameter. The catheter body includes a distal portion 126, typically being between 2.2 and 3.0 F, and first and second enlarged portions 128, 130. First and second enlarged portions 128, 130 reduce the pressure required for the introduction of clear flush around the falloposcope 14, as is more fully explained in co-pending U.S. patent application Ser. No. 08/207,475, the full disclosure of which has previously been incorporated by reference. A Touhy-Borst valve 132 is provided near the proximal end of the catheter to seal the proximal end and also allow access for falloposcope 14. An irrigation port 134 is also provided.

A particularly advantageous structure for supporting distal guidewire 122 comprises a distal ring coupler 125 which is fittingly inserted within distal portion 126 of guidewire catheter 120. The ring coupler provides effective support for the guidewire, but does not increase the proximal size or stiffness of the catheter body, and also maintains a smooth outer surface. Typically, the coupler ring and guidewire will comprise stainless steel, platinum, or a shape memory alloy such as Nitinol™, or the like. The guidewire will typically be coiled, but will ideally include an uncoiled portion extending to internal coupler ring 125, thereby minimizing the blockage of the catheter lumen.

Distal guidewire 122 is offset distally at an edge of guidewire catheter 120, and thereby allows the rotational engagement of the tubal wall described above regarding FIG. 7. Advantageously, the guidewire blocks the smallest possible imaging area, and also provides increased functionality for the catheter by allowing the catheter to be self-guided during introduction. Furthermore, the central lumen is not occupied by a conventional guidewire during advancement of the catheter into the fallopian tube, thereby providing the attending surgeon the option of advancing the falloposcope to the viewing position of guidewire catheter 120 to visually direct catheter advancement.

Figure 11A:
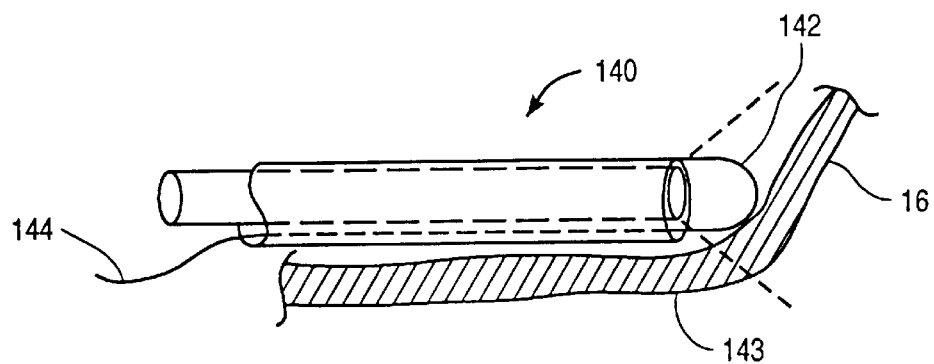
FIGS. 11A, B, C, and D illustrate access catheters having a guidewire which extends from the distal end of the catheter body to form a distal loop, which distal loop can be expanded by axially advancing a proximal extension of the guidewire, in accordance with the principles of the present invention.
Figure 11B:
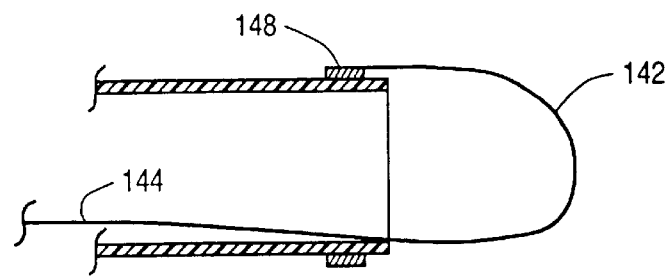
Figure 11C:
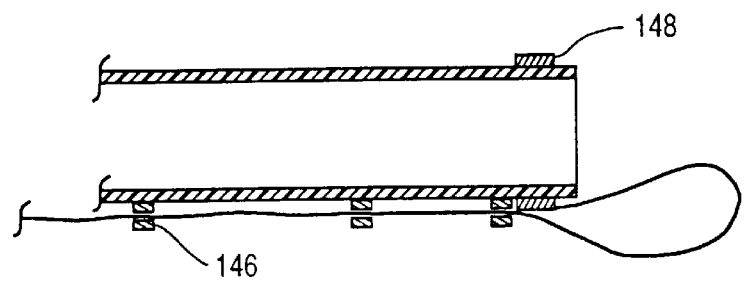
Figure 11D:
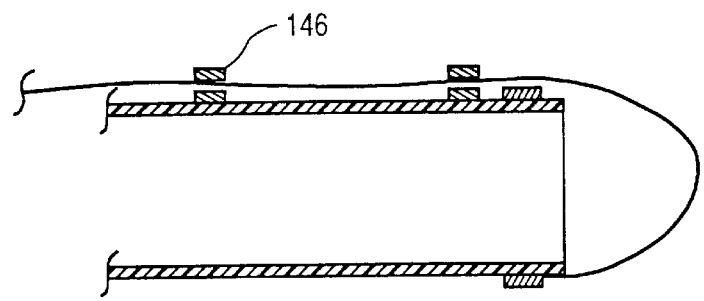
Figure 14A:
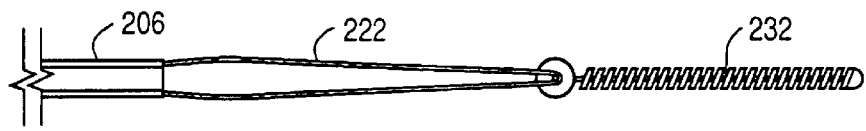
FIGS. 14A–H illustrate a variety of alternative flexible caged access catheters according to the principles of the present invention.
Figure 14B:
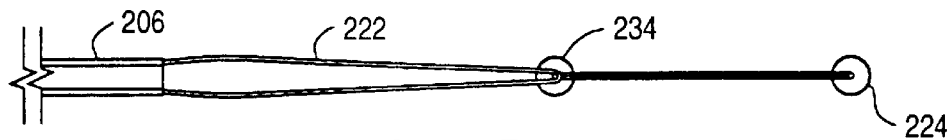
Figure 14C:
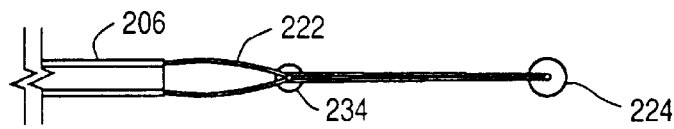
Figure 14D:
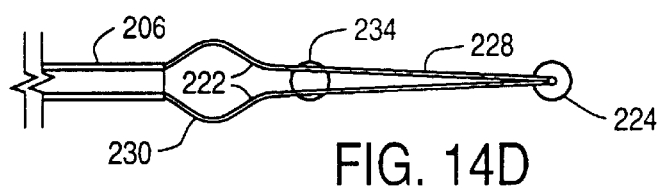
Figure 14E:
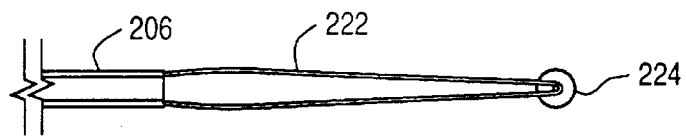
Figure 14F:
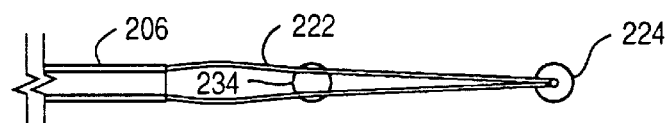
Figure 14G:
Figure 14H:

Referring now to FIGS. 11A through D, a looped guidewire access catheter 140 generally comprises a guidewire which extends distally from a distal catheter body end 143, the guidewire forming a distal loop 142. A proximal extension 144 of the guidewire runs along the length of the catheter body, allowing the distal loop to be manipulated by axially advancing and retracting extension 144 relative to the proximal end of the catheter body. As shown in FIGS. 11B through D, extension 144 may be disposed within the lumen of the catheter body, or may alternatively pass through guides 146 on the outer surface of the catheter. Alternatively, a separate lumen may be included in the catheter body, although this will require an increase in the cross-sectional size of the catheter. The guidewire may be attached to the distal end of the tip using coupler ring 125 (FIG. 10C), or may alternatively extend from a distal outer ring 148, or from the catheter lumen wall itself.

Advantageously, distal loop 142 provides an active mechanism for the surgeon to control the separation between the tubal wall and the falloposcope. By advancing extension 144 distally only when a white-out condition occurs, the distance between the tubal wall and the scope may be varied without having to move the scope itself. The guidewire loop may further be retracted when not in use, and may also be biased to assume a particular distal shape, as seen in FIG. 11C.

Figure 12A:
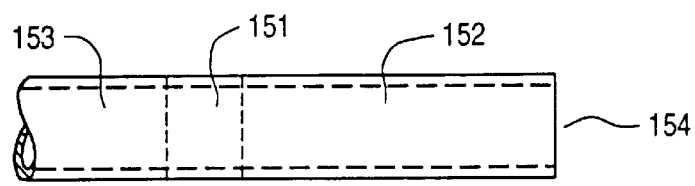
FIGS. 12A and B illustrate an access catheter having an extended diagonal tip formed by joining different tubes and cutting the joined tubes along a curve.
Figure 12B:
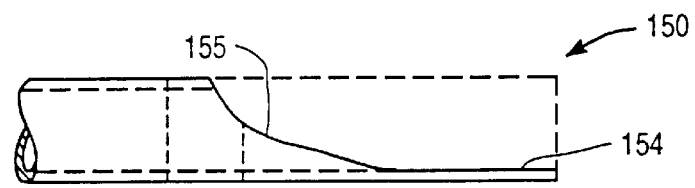

FIGS. 12A and B illustrate a particularly advantageous access catheter 150 which is formed by joining an intermediate tube 151 and an end tube 152 to catheter body tubing 153. The tubes may be adhesively bonded, or preferably melted together. The diameter of the tubing increases toward the distal end 154. A curved cut forms an extended diagonal tip 157. Proper selection of tubing material, together with careful shaping of the extended tip 157, provides control over the flexibility of the distal structure. Clearly, the tip shape may comprise a smooth curve or a series of angles, and any number of tubing sections may be joined, within the scope of the present invention. Advantageously, extended diagonal tip 157 provides the functionality of a distal guidewire, but with an easily fabricated, uninterrupted structure.

Referring now to FIG. 13, a preferred embodiment of a caged access catheter 200 has a proximal end 202 and a distal end 204. A catheter body 206 extends distally from near the proximal end to a tracking cage 208. A valve assembly 210 at the proximal end of catheter body 206 provides sealing, and will generally include an irrigation port 212. The valve assembly will typically be attached using a strain relief coupling 214, as is generally known in the art.

The catheter body 206 will include a relatively large diameter proximal portion 216 and a smaller diameter distal portion 218, the distal portion preferably being at least about 3 inches long. Catheter lumen 220 will typically range between about 0.015 and 0.05 inches in diameter, often being smaller in the distal portion 218 than in the proximal portion, as described above. The catheter body will generally have an outer diameter of between about 0.020 and 0.075 inches, and a total length of between about 8.0 and 25.0 inches. The smaller diameter distal portion will preferably be between about 4.0 and 7.0 inches in length.

Cage 208 comprises a plurality of axially oriented cage elements 222 which extend distally from the distal end of catheter body 206. Preferably, cage elements 222 have both high strength and high flexibility, ideally comprising a shape memory alloy such as Nitinol™ with super-elastic properties when at body temperature. A tracking tip 224 is disposed at the distal ends of the cage members, the tracking tip having a relatively large rounded distal surface. The tracking tip may be formed from a wide variety of polymer or metallic materials, preferably comprising a shape memory alloy, urethane, adhesive, solder, or the like. In many embodiments, the cage elements are affixed together at the tracking tip to maintain the structural integrity of the cage.

Referring now to FIG. 13A, the cage elements are generally disposed radially about the distal end of catheter body 206. Preferably, there are at least four cage elements surrounding the scope, so that the cage effectively maintains separation between the distal end of the scope and a surrounding tubal wall 226 even when the tubal wall protrudes somewhat inward between cage elements. The use of four or more cage elements also minimizes the effect of any rotational misalignment or deformation of the cage elements. In other words, if two adjacent cage elements are at roughly 90° as shown, each can spread by 15° and the adjacent cage elements will still be separated by only 120°, generally close enough to prevent the lumenal wall from encroaching too close to the scope. Hence, even when the cage is distorted, as when navigating a tight luminal curve, a cage of four or more axial elements can generally avoid white-out.

Referring now to FIG. 13B, cage elements 222 extend proximally along catheter body 206, typically being affixed around the catheter body by heat-shrink tubing or the like. In some embodiments, the cage elements may extend distally from the catheter body to tracking tip 224, and then bend back to the catheter body. Such bent caged elements help maintain the structural integrity of the cage at the tracking tip, and are particularly beneficial for use with tracking tips formed of polymer materials such as urethane. A tracking tip making use of bent cage elements is illustrated in FIG. 13C.

Referring now to FIG. 13D, cage 208 preferably includes a highly flexible distal portion 228 of relatively small cross-section, and a radially outward flared proximal portion 230 adjacent catheter body 206. The flared portion helps to center the scope within larger portions of the body lumen, and perhaps more importantly, the flare prevents the luminal wall from encroaching on the scope when the cage flexes to traverse bends in the body lumen. The distal portion of the flare may also help to hold a portion of the luminal wall (in particular, that portion which is at the proper focal distance and within the field of view from scope) at a steeper angle, thereby improving the image of the tissue surface. The cage will typically extend distally from the catheter body by a total of between about 0.5 and 1.5 centimeters.

Flared portion 230 will typically protrude radially beyond the adjacent catheter body, typically extending between about 0.02 and 0.05 inches radially beyond the adjacent portions of the cage. The cage ideally tapers radially inward distally from the flared portion to the tracking tip, the narrow cross-section helping to enhance the axial flexibility of the cage structure. The tracking tip also protrudes radially beyond the adjacent cage cross-section so that the tracking tip will slide over irregularities in the lumenal surface, but is generally no larger than the distal end of catheter body 206.

A variety of alternative cage structures are illustrated in FIGS. 14A–H. Optionally, a coil 232 may extend distally to act as a conventional guidewire tip. In some embodiments, an intermediate body 234 may help minimize separation and maintain structural integrity of the cage surrounding the scope. Cage elements 222 may optionally define a rounded distal bend 236, thereby providing an atraumatic distal surface without having a separate tracking tip body. Alternatively, a pointed cage end 238 defined by sharp bends in cage elements 222 may be advantageous for certain applications. In summary, the distal tip can be formed to the specific geometry desired, and the cage may include additional axially oriented or transverse cage elements.

Similarly, a wide variety of rounded tip bodies may be used as tracking tips. However, it should be recognized that as the number of cage elements increases, the discreet number of areas blocked from view when imaging the lumenal walls will also increase, imaging being performed through the openings defined between cage elements. While a relatively large tracking tip may block some portion of the image, the tip itself may be outside the field of view from the scope when used within tortuous narrow body lumens such as the fallopian tubes, and may be outside the focal range of the scope when it is not otherwise blocked. In other embodiments, it may be advantageous to have the tracking tip within the image provided by the scope, so that axial advancement of the catheter may be directed while viewing the proximal portion of the tracking tip body.

Figure 15A:
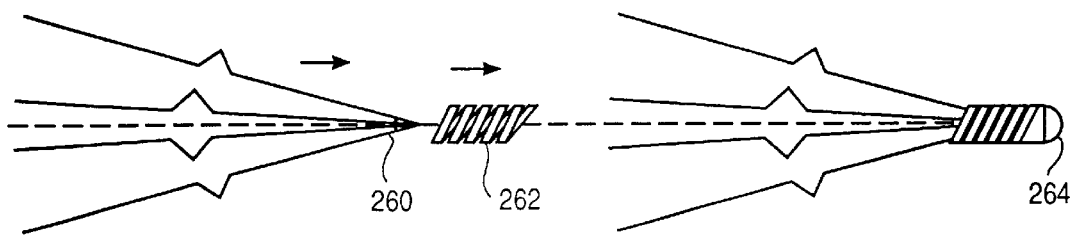
FIGS. 15A and B illustrate alternative methods for securely attaching a tracking tip body having a rounded surface at the distal end of a flexible cage by winding subcoils over the cage elements, and then soldering an outer coil over the distal end so that the solder forms the distal rounded surface.
Figure 15B:
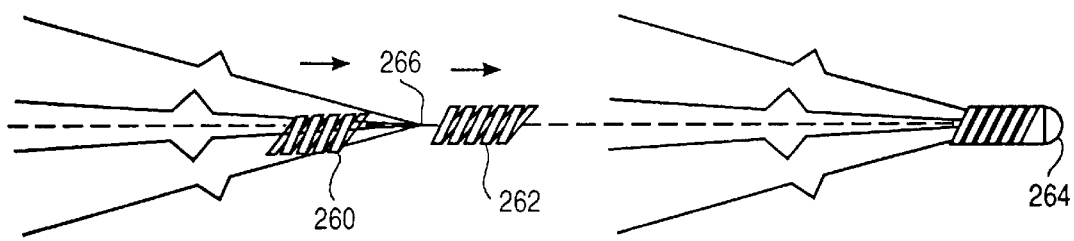

Referring now to FIGS. 15A and B, the strength of the junction formed at the tracking tip may be enhanced by winding sub-coils 250 around some or all of the cage element distal ends, particularly when the tracking tip comprises solder. Optionally, the sub-coils are then inserted within an outer coil 262. This outer coil facilitates the formation of a rounded distal tracking tip surface 264 from the molten metal. Alternatively, a single sub-coil 260 may be wound around a plurality of the ends of a bent cage structure adjacent the distal bend 266, ideally around three of the four ends as illustrated in FIG. 17B. Such coils and sub-coils generally comprise small ribbons of a high strength metal such as platinum.

Figure 16:
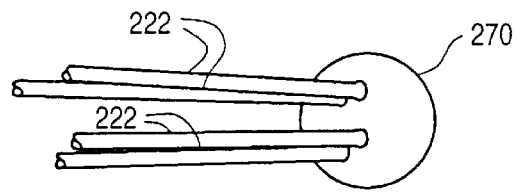
FIG. 16 illustrates an alternative tracking tip formed by melting the distal ends of the flexible cage elements using thermocouple forming techniques.

Referring now to FIG. 16, a particularly advantageous distal tracking tip 270 may be formed and attached by melting the material of the cage elements themselves. Conveniently, techniques commonly used for forming thermocouples have been found to form such a structure. Thermocouples are often produced by forming an electrical arc between a first surface and the ends of a plurality of wires, the arc heating the wire ends to form a molten ball. Thermocouple welders for production of these structures are commercially available from the Unitek Miyachi Corp. of Monrovia, Calif. It has been found that by clamping a plurality of metallic cage elements in the desired configuration, such a thermocouple welder is capable of producing an integral tracking tip at the ends of all of the cage elements in a single step, even where the cage elements comprise a shape memory alloy.

Figure 17:
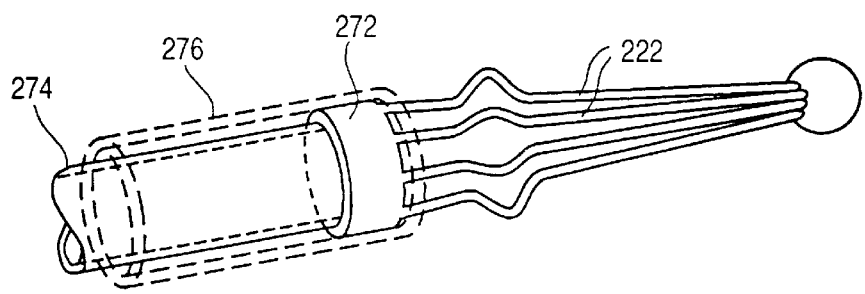
FIG. 17 illustrates an alternative distal cage having a proximal collar to facilitate attachment of the cage to the catheter body.

Referring now to FIG. 17, it may be advantageous to join the proximal ends of cage elements 222 to a ring 272 as illustrated. Preferably, ring 272 is affixed to the catheter body by laminating the ring between an inner catheter 274 and a shrink wrap tubing 276. These inner and outer layers are preferably bonded together distally of ring 172. Nonetheless, the length of the catheter body which is axially stiffened by the ring of the cage may be less than the embodiment of FIG. 13, in which each of the cage elements are bonded individually to the catheter body. Such individual cage element/catheter body bonds (as shown in FIG. 13) typically include an overlap of between about 0.1 and 0.9 inches to prevent the cage elements from being pulled out distally.

Figure 18A:
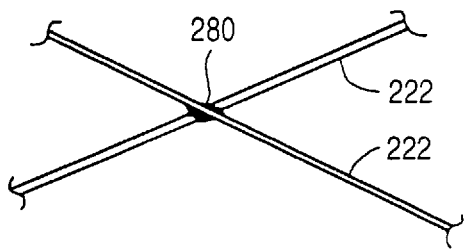
FIGS. 18A and B illustrate methods for producing a caged access catheter in which the cage elements are joined to each other prior to attachment to the catheter body, either before or after the caged elements are bent to their final shape.
Figure 18B:
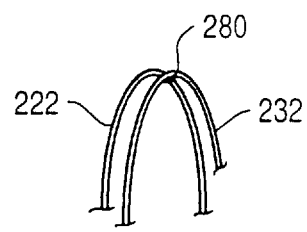

FIGS. 18A and B illustrate methods for fabricating imaging separation cages by forming a spot weld 180 at the distal junction of cage elements 222. Junction 180 may be formed either before the cage elements are bent to shape (as shown in FIG. 18A), or after bending the cage elements (as in FIG. 18B).

Figure 19A:
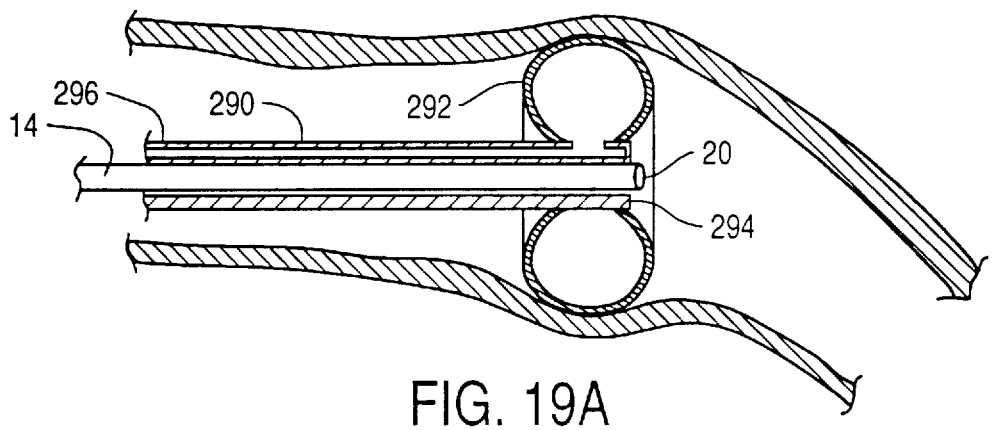
FIG. 19A illustrates an alternative access catheter according to the present invention in which a toroidal balloon disposed at the distal end of the catheter maintains separation between the luminal wall and the distal end of the scope.
Figure 19B:
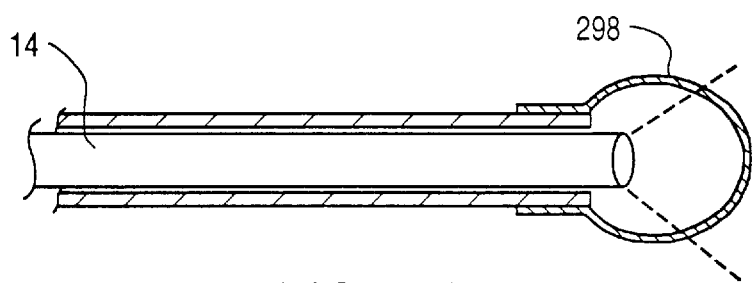
FIG. 19B illustrates an alternative catheter according to the principles of the present invention in which an optically transparent balloon maintains separation between the scope and the luminal wall while the luminal wall is imaged through the balloon membrane.

Referring now to FIG. 19A, a toroidal balloon separation catheter 290 includes a toroidal balloon 292 adjacent the catheter's distal end 294. A balloon inflation lumen 296 allows the balloon to be inflated to maintain separation between the scope and the adjacent luminal wall. Alternatively, an optically transparent balloon 298 may be disposed over the end of the catheter body as illustrated in FIG. 16B. Transparent balloon 298, typically comprising silicone or the like, may advantageously expand folds and wrinkles in the luminal wall, thereby exposing surfaces which might otherwise be difficult to image.

The enhanced trackability of the access catheter of FIG. 13, as provided by the rounded distal surface and flexible cage, can be understood with reference to FIGS. 20–22A. The relatively large rounded surface of tracking tip 224 slides over the inner surface of tubal wall 16, and is not easily entrapped within minor irregularities in the lumenal surface. Where the body lumen is larger than the catheter body, as in FIG. 21, flared portion 230 of cage 208 helps keep the scope centered within the body lumen, facilitating imaging of the entire perimeter. The cage also flexes resiliently to accommodate bends in the lumenal axis. Even when flexed, however, the radially protruding flared portion 230 prevents the lumenal wall from encroaching too close to the scope. As the body lumen narrows, flared portion 230 gently and resiliently distends the lumenal wall, ideally holding a portion of the lumenal wall at an angle suitable for imaging from the scope, as seen in FIGS. 22 and 22A. By distally advancing the scope and the access catheter, and by flowing irrigation fluid through the catheter lumen and over the scope, antigrade imaging of the fallopian tubes with good image quality will be possible. Such antigrade imaging will eliminate the need to first position a guidewire in the distal fimbria, advance a catheter over the guidewire, and replace the guidewire with a scope, and thereby greatly facilitates the optical imaging of fallopian tubes and other narrow body lumens. The scope may also provide an image of an occlusion or lumenal bend which impedes axial advancement of the scope, allowing advancement to proceed under optical direction.

Figure 23:
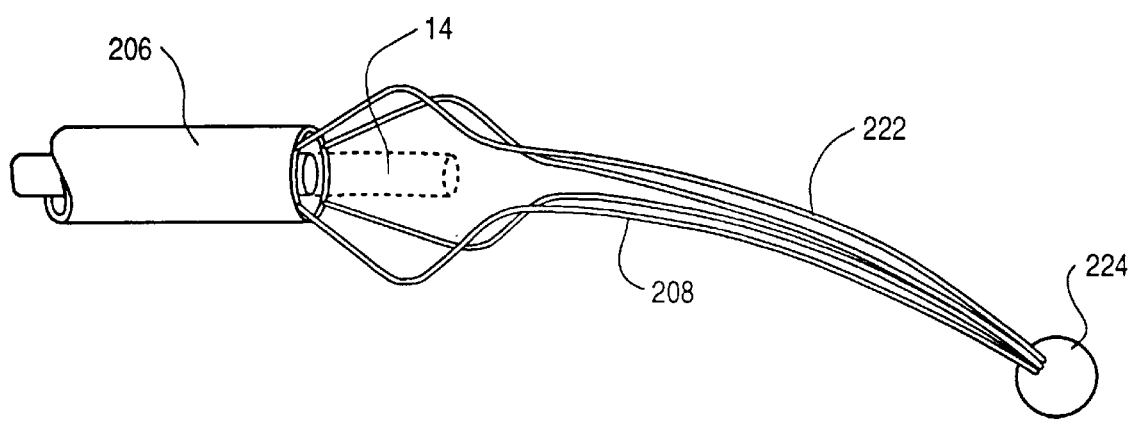
FIG. 23 illustrates a flexible access catheter similar to the preferred access catheter of FIG. 13 in which the cage is bent to function as a steerable guidewire, and also illustrates axial manipulation of the scope within the cage to provide enhanced imaging flexibility, according to the principles of the present invention.

Referring finally to FIG. 23, in some embodiments of the present invention, manipulation of scope 14 independently of the access catheter allows imaging of selected portions of the tubal wall while they are held in a fixed position by the cage 208. Additionally, cage 208 may be bent to help guide the access catheter distally around sharp body lumen bends, or to maneuver the access catheter through branching body lumen systems. Optionally, the bend may be pre-formed and the access catheter rotated to the desired angular orientation under the direction of the optical image provided by the scope. Alternatively, one or more of cage elements 222 may extend slidably along the catheter body to a handle, thereby allowing remote manipulation of the cage to provide steering.

Still further optional features may be included within the scope of the present invention. For example, tracking tip 224 might include a radially oriented ultrasound transducer to measure lumenal wall thickness. In alternative embodiments, one or more of the cage elements may include optical illumination fibers, thereby providing illumination for the scope from the cage or from the tracking tip. Therefore, although the foregoing invention has been described in some detail by way of illustration and example, for purposes of clarity and understanding, it will be obvious that certain changes and modifications may be practiced within the scope of the appended claims.

What is claimed is:

1. A catheter for viewing a wall of a narrow body lumen in combination with an optical viewing scope, the catheter comprising:
    an elongate tubular body having a proximal end, a distal end, and a lumen therebetween; and
    a spacing structure comprising a plurality of cage elements extending distally from the distal end of the tubular body, the cage elements adjacent the distal end of the tubular body protruding radially beyond the body cross-section, the spacing structure adapted to maintain separation between the scope and the surrounding lumenal wall when the scope images the body lumen between the cage elements, at least a distal portion of the spacing structure being flexible.

2. A catheter as claimed in claim 1, wherein the spacing structure is adapted to track along bends in the body lumen when axially advanced therein.

3. A catheter as claimed in claim 1, wherein the spacing structure has a cross-section along the flexible portion which is smaller than a cross-section of the tubular body, the spacing structure further comprising a tracking tip having a rounded distal surface which is larger than the flexible cross-section.

4. A catheter as claimed in claim 3, wherein the cage elements are affixed to the tracking tip of the spacing structure.

5. A catheter as claimed in claim 3, wherein the cage elements extend distally from the tubular body to the tracking tip, and bend proximally at the tracking tip back toward the tubular body.

6. A catheter as claimed in claim 5, wherein the tracking tip comprises a material selected from the group consisting of solder, polymer, and material from the cage elements.

7. A catheter as claimed in claim 1, wherein at least four axial elements are distributed around the lumen at the distal end of the tubular body.

8. A catheter as claimed in claim 1, wherein the axial elements comprise a shape memory alloy.

9. A fallopian tube viewing system for imaging a tubal wall of a fallopian tube, the viewing system comprising:
    a falloposcope having a proximal end, a distal end, and an axis therebetween;
    an access catheter having an elongate tubular body with a proximal end, a distal end, a lumen therebetween which slidably receives the falloposcope, a flexible separation structure extending distally from the distal end of the tubular body around the lumen to maintain separation between the scope and the surrounding tubal wall when the scope is disposed within the lumen of the access catheter, at least a distal portion of the cage elements angling distally inward toward the axis, when the scope and catheter are disposed within the fallopian tube, and when the body lumen is imaged through the separation structure, and a tracking tip which protrudes radially beyond the adjacent cage elements.

10. A viewing system as claimed in claim 9, wherein a proximal portion of the cage elements angle distally outward away from the axis.

11. A method for manufacturing a caged access catheter, the method comprising:
    attaching a plurality of flexible elongate cage elements to each other at a junction;
    forming a tracking tip at the junction after the attaching stop, the tracking tip having a distally oriented rounded surface which is larger than combined cross-sections of the cage elements; and
    affixing the cage elements about a lumen of a tubular body so that the elongate elements extend distally from the tubular body.

12. A method as claimed in claim 11, further comprising bending the cage elements so that opposed ends of the cage elements extend proximally from the junction.

* * * * *